United States Patent [19]

Bull et al.

[11] Patent Number: 5,316,949

[45] Date of Patent: May 31, 1994

[54] METHOD OF DETECTING THE PERMEABILITY OF AN OBJECT TO OXYGEN

[75] Inventors: Christopher Bull, Bethesda, Md.; Charles R. Barmore, Moore, S.C.

[73] Assignee: W. R. Grace & Co.-Conn., New York, N.Y.

[21] Appl. No.: 988,511

[22] Filed: Dec. 10, 1992

[51] Int. Cl.$^5$ ............................................. G01N 31/00
[52] U.S. Cl. .......................................... 436/5; 436/1; 436/127; 436/138; 436/904; 422/56; 422/86
[58] Field of Search ............... 436/127, 903, 136, 904, 436/138, 1, 5; 422/56, 86, 88, 83, 84

[56] References Cited

U.S. PATENT DOCUMENTS

| | | | |
|---|---|---|---|
| 3,725,658 | 4/1973 | Stanley et al. | 250/71 R |
| 3,768,976 | 10/1973 | Hu et al. | 23/254 R |
| 4,169,811 | 10/1979 | Yoshikawa et al. | 252/408 |
| 4,478,792 | 10/1984 | McConnaughey et al. | 422/86 |
| 4,526,752 | 7/1985 | Perlman et al. | 422/56 |
| 4,657,736 | 4/1987 | Marsoner et al. | 422/56 |
| 4,659,674 | 4/1987 | Bauman et al. | 436/5 |
| 4,810,655 | 3/1989 | Khalil et al. | 436/136 |
| 5,096,813 | 3/1992 | Krumhar et al. | 422/56 |
| 5,104,811 | 4/1992 | Berger et al. | 422/56 |
| 5,107,696 | 4/1992 | Mayer et al. | 73/38 |
| 5,155,046 | 10/1992 | Hui et al. | 436/136 |

OTHER PUBLICATIONS

Fisher Scientific Catalog, 1988 p. SDS 261C.
"Fluorometric Analyses of Riboflavin and Its Coenzymes"; Jacek Koziol; Methods in Enzymology, vol. XVIII, Vitamins and Coenzymes; 1971, pp. 253–285.
"Photochemistry of Flavins"; G. R. Penzer and G. K. Radda; Methods in Enzymology, vol. XVIII, Vitamins and Coenzymes; 1971; Part B, pp. 479–495.

Primary Examiner—James C. Housel
Assistant Examiner—Lien Tran
Attorney, Agent, or Firm—Valerie E. Looper

[57] ABSTRACT

A method of detecting the permeability of an article to oxygen is disclosed. A fluorescent redox indicator, preferably riboflavin, is dispersed in a carrier and placed on an impermeable substrate. The article to be measured is placed adjacent to the carrier. Residual oxygen is removed, the redox indicator is photoreduced, the article and carrier are exposed to oxygen, and the indicator is exposed to UV light.

9 Claims, 8 Drawing Sheets

METHOD OF DETECTING THE PERMEABILITY OF AN OBJECT TO OXYGEN

FIELD OF THE INVENTION

This application relates to a method of detecting the oxygen permeability of an article. This method allows the detection of flaws in an oxygen barrier such as pinholes and cracks, as well as the overall permeability over time. Further, this method can be re-used several times to show whether the oxygen barrier's characteristics change over time. The method is easy to set up and use, and provides quick results. Compared to the available technology, this method is far cheaper, and yields an order of magnitude increase in sensitivity. Unlike available technology, this method can spatially resolve the permeability of an object, i.e., detect streaks, cracks, pinholes and other features. Also, this method more closely correlates with the real-world use for which it was originally developed, to test a food wrap, since it uses a food simulant and ambient temperature, pressure, humidity and gas mixtures for test conditions.

BACKGROUND OF THE INVENTION

It has been found that polymeric materials can be drawn into thin, transparent films. When this is done, however, it is difficult to tell whether the film has been properly made, or whether it has flaws, especially if the film has multiple layers. Many critical flaws are not visible. Hand calibration of thickness is not feasible. The standard analytical instrument for measuring oxygen permeability, as described in U.S. Pat. No. 5,107,696, can only detect average permeability over an area typically five square inches.

Various methods of measuring the presence of oxygen are known for use in various systems. Liquid systems are discussed in U.S. Pat. No. 4,659,674 issued to Bauman et al., Apr. 21, 1987, which discloses an ion-specific electrode. The possibility of determining oxygen permeation via pH change is discussed but only overall permeability is disclosed, and surface flaws such as pinholes in a barrier could not be detected.

The amount of oxygen in a gaseous stream has also been measured. For example, U.S. Pat. No. 3,725,658, issued to Stanley et al., Apr. 3, 1973, relates to a medical oxygen analyzer. It discloses an apparatus and method for continuously detecting rapid changes in the oxygen content of a gas stream; that is, a total response time of not more than 0.1 seconds per measurement. The reference relies on the use of a fluorescent material such as pyrene, coronene and p-terphenyl whose fluorescence is partially quenched by the presence of oxygen. Elaborate mechanical support is required. There is no spatial resolution of oxygen flow.

Oxygen detectors have been used in packaging. U.S. Pat. No. 4,526,752, issued to Perlman, Jul. 2, 1985, relates to a tamper-resistant package. A dye, such as methylene blue, which is colorless in the reduced state and becomes colored upon exposure to oxygen is dissolved in water along with a volatile reducing agent. The reducing agent is removed, along with the water, preferably under vacuum, and the package is sealed. If the package is broken, the dye will become colored upon exposure to air. The change in color of the package is irreversible.

Another type of oxygen detector is used in U.S. Pat. No. 3,768,976, issued to Hu et al. Oct. 30, 1973, which relates to a temperature-time indicator for food packaging. The indicator is a film package that contains an aqueous solution of a redox dye such as sodium anthraquinone beta-sulfonate. The dye in its reduced state is dark red and obscures a warning message. As oxygen permeates into the package in an amount which is dependent on temperature and time, the dye fades and the warning message is revealed. This system is not reversible, and spatial resolution of the rate of oxygen permeation is not disclosed or discussed.

Similarly, U.S. Pat. No. 4,169,811, issued to Yoshikawa Oct. 2, 1979 discloses an oxygen indicator which is a dye, a base, and a reducing agent. The dye has one color in an anaerobic environment and another color in an aerobic environment. These dyes are derivatives of methylene blue. It is disclosed that these dyes require the presence of water or an alcohol in order to function. The reducing agents are disclosed to be saccharides, dithionites and ferrous compounds. The oxygen sensitivity is disclosed to be as low as 0.1% [column 6, line 65].

A probe is disclosed in U. K. Patent Application 2132348A, which relates to the use of platinum group metal complexes which luminesce when excited by visible or UV light, and which are quenched by oxygen and other materials. A sensor, which incorporates the metal complex in a carrier, which must be permeable to oxygen and relatively impermeable to other quenchers is exposed to the environment and oxygen permeates the carrier and partially quenches the fluorescence of the metal complex. The quenching-related decrease in intensity or lifetime of luminescence is measured and correlated to the presence of oxygen. The precision and accuracy is about 2 percent. Spatial resolution of oxygen permeability is not disclosed. The use of a sensor akin to pH paper is discussed, which is said to yield only semi-quantitative or qualitative oxygen monitoring (Col. 8, lines 116-126).

The difficulty with many indicators is that they are not physically compatible with the most likely carriers. U.S. Pat. No. 4,657,736, issued to Marsoner et al. Apr. 14, 1987, addresses this point, disclosing that fluorescent indicators can be reacted with tertiary butyl chloride to render them compatible with silicone polymer carriers to avoid having the indicator crystallize out of the polymer.

What is needed is a method of detecting oxygen transmission through a barrier that is useful for quality control in day-to-day manufacture of polymer sheets and other objects, and for design and development of new oxygen barrier materials. The method should be relatively quick and be both qualitative and quantitative. It should also be activated on demand and capable of detecting manufacturing defects such as streaks and pinholes.

Although this application is written in terms of a specific end use, one of ordinary skill in the art will readily recognize that it is a general tool for detecting cracks and pinholes wherever oxygen might be used as an indicator. For example, it could be used to detect flaws in sheets of aluminum foil. In that case, oxygen permeability per se might not be the primary interest, if one is interested in the physical integrity of the foil. Similarly, the integrity of opaque or tortuous path type materials such as ceramics could be tested as well.

The inventors have found that a system based on the reaction of a redox indicator can be used to measure oxygen transmission in great physical detail, that is, make an image of a barrier's permeability. This Low Oxygen Transmission Imaging System ("LOTIS") can be used in both qualitative and quantitative modes.

It is, therefore, an object of this invention to provide a method and apparatus for detecting the rate of permeation of oxygen through a barrier at various locations.

Another object is to provide as the detecting component for oxygen analysis a stable sheet comprising a redox compound dissolved in a solvent or carrier, which sheet is supported on a substrate and is re-usable.

A particular advantage of the present invention is that the redox compound and carrier can be stored indefinitely under ambient, that is, oxygenated conditions. Previous systems using chemical reductants and redox dyes had to be prepared and used fresh due to their oxygen reactivity.

SUMMARY OF THE INVENTION

To use this invention, a redox indicator is dispersed in a carrier and placed on a support which is not a potential oxygen source. The barrier which is being tested is placed next to the indicator to make a sandwich structure or plate. It is preferred that residual oxygen in the carrier and barrier themselves be removed. This can be conveniently done by flushing with nitrogen, or a vacuum treatment of the plate (or both), followed by photoreduction. To photoreduce the indicator, the plate is exposed to UV light or any ambient fluorescent or incandescent light for an empirically determined period of time. For a 40 watt cool white fluorescent fixture at a distance of about two feet from the test article, times of about thirty minutes to an hour will be adequate. The photoreduced plate is now essentially devoid of fluorescence because the riboflavin is in a photoreduced state. Examining the plate under UV light will confirm the lack of fluorescence.

In order to measure the permeability of the object to oxygen, the plate is allowed to equilibrate under ambient conditions in the dark for a predetermined time. Then the plate is then exposed to UV light to excite the fluorescence of oxidized riboflavin. Areas of relatively low permeability will be dark, while areas of higher permeability will show a brighter fluorescence. The position of streaks, pinholes and surface artifacts can be resolved to a location within an area of 1/16 square inch. It is important to the quantitative practice of this invention that the light used to read the fluorescence of the plate is of such an intensity and duration that it does not cause significant photoreduction.

Figure 1:
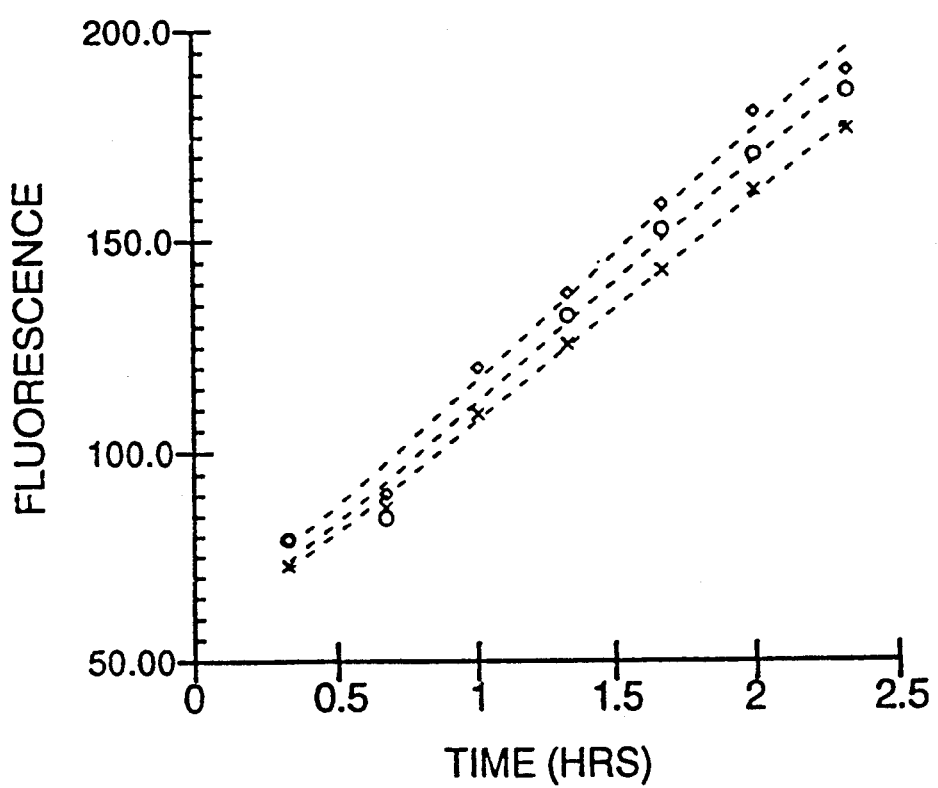
FIGS. 1-4 are graphs of the fluorescent levels for film samples A-D.
Figure 2:
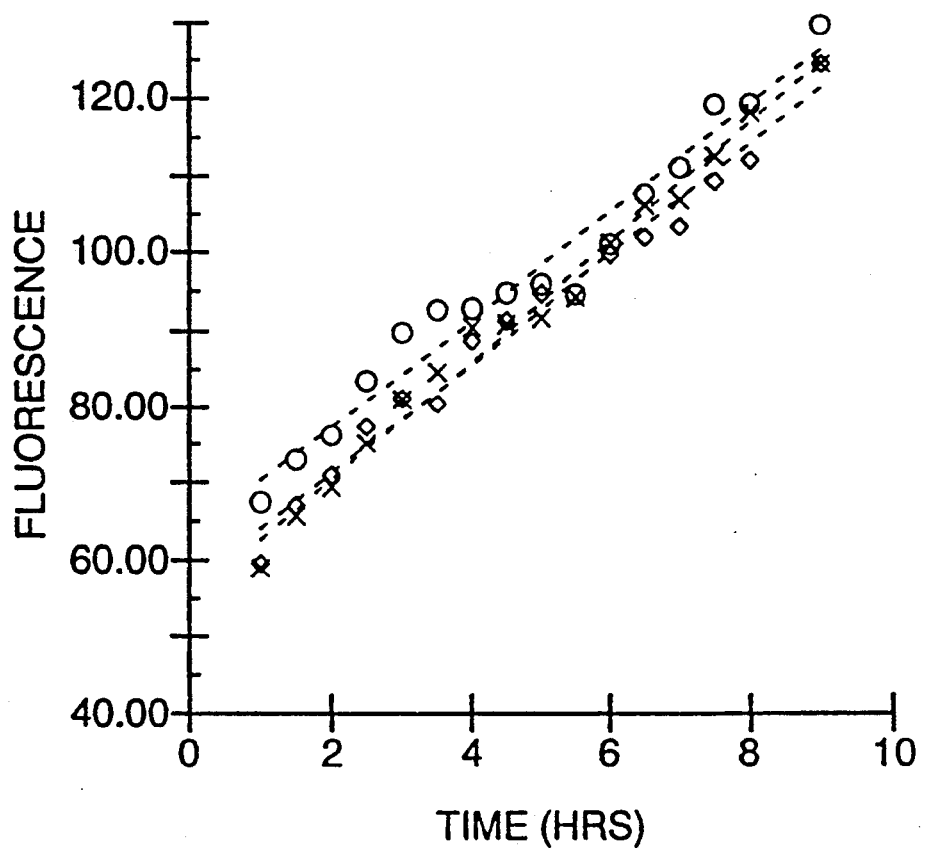
Figure 3:
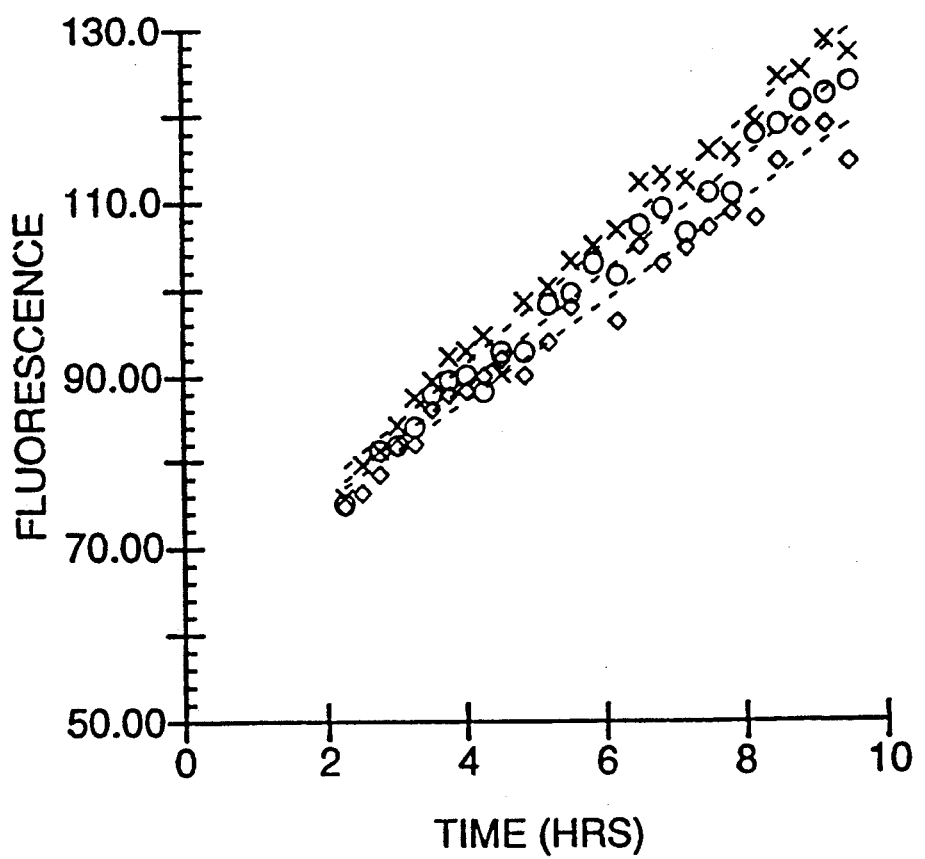
Figure 4:
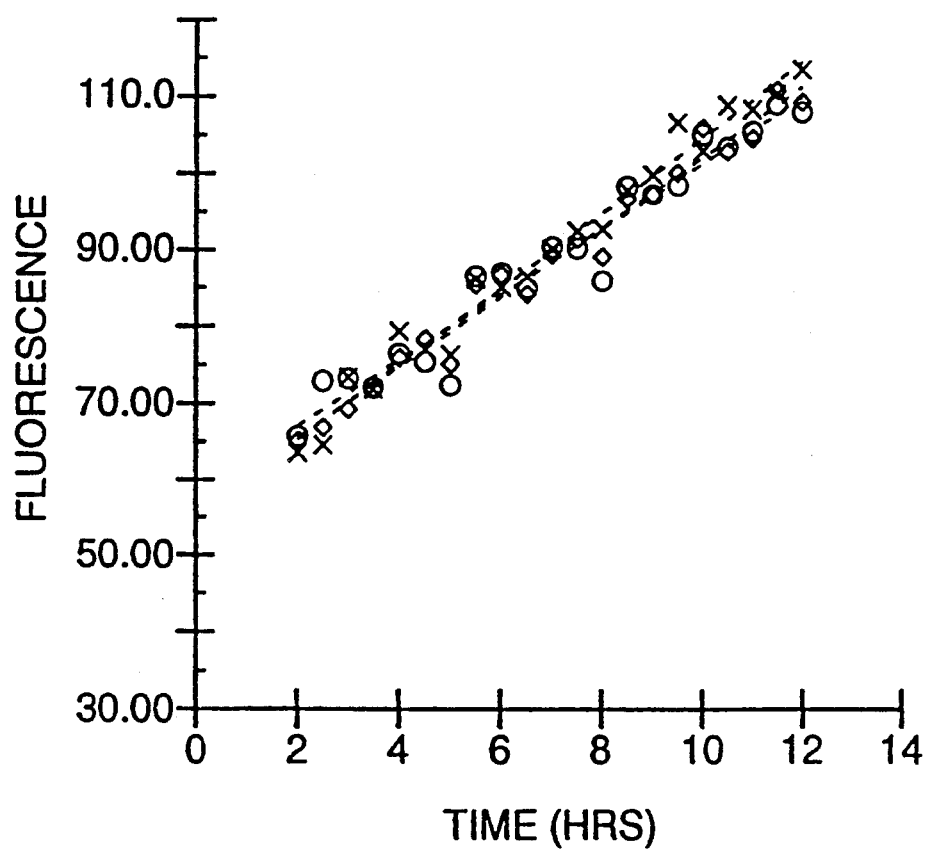

A system based on riboflavin as the redox indicator is preferred because
  1) Riboflavin exists in two redox states: an oxidized, highly fluorescent state and a reduced, much less fluorescent state. This second state exhibits a weak fluorescence at a different wavelength from the first, which is easily removed with suitable filters.
  2) Riboflavin is photoreduceable in the presence of a sacrificial photoreductant such as ethylenediaminetetraacetic acid ("EDTA") or oxalate. "Photochemistry of Flavins", Penzer & Radda, *Methods in Enzymology*, Vol. XVIII, part B, pp. 479-495, Academic Press, N.Y., (1971). Photoreduction is important in this context because it yields a significant advantage over chemical reduction methods. It should be noted that EDTA does not reduce riboflavin in the absence of light. The plates can be activated upon demand. In addition, once the riboflavin is reduced, there is no excess chemical reductant present. The subsequent reoxidation reaction is known to be quantitative. "Fluorometric Analyses of Riboflavin and Its Coenzymes", Kozoil, *Methods in Enzymology*, Vol. XVIII, part B, pp. 253-285:256, Academic Press, N.Y., (1971).
  3) Reduced riboflavin is highly reactive with oxygen to regenerate the oxidized state. Also, in the context of this invention, once the oxygen is reacted, it is trapped and little diffusion occurs. Images which are made using this method are relatively sharp.
  4) Riboflavin, (also known as Vitamin B-2) is biocompatible, and so its use does not present environmental concerns.

This system is described in terms of riboflavin because it is a redox indicator particularly suitable for the inventors' purposes. One of ordinary skill in the art will readily recognize that other redox systems are usable, particularly for non-food applications.

The carrier is preferably some easy-to-handle gel such as gelatin, cornstarch, agar, etc. One of ordinary skill in the art will recognize that any solid or liquid in which the redox indicator is dispersible, and which has desirable handling properties, can be used.

The support is any sheet of material which is less permeable to oxygen than the test article, does not fluoresce, and which has appropriate handling properties for the application. Appropriate supports could be glass or plastic plates, or flexible films.

The sacrificial reductant can be any organic aliphatic amine or amino acid that will function as an electron source, i.e., is capable of being oxidized. Of these, ethylenediaminetetraacetic acid and triethylamine may be mentioned. Sugars will work, as well as riboflavin itself and various flavin derivatives, and also alcohols.

Accelerators can also be added, of which a buffer such as trisodium citrate dihydrate is an example. In this context, an accelerator will speed up the photoreduction step, resulting in a shorter testing time. Up to about 3% by weight can be used.

Scattering agents can also be used to increase the fluorescent response. Any particulate or fibrous material can be used. Titanium dioxide and finely ground silica gel particles or paper fiber can be used. In addition, other additives such as antifoam and mold inhibitors may be added.

In one embodiment of the present invention, a piece of absorbent paper is saturated with a warm gelatin mixture:

| Ingredient | % by weight |
|---|---|
| Riboflavin | 0.01 |
| Gelatin | 7.0 |
| Disodium EDTA | 0.7 |

The indicator paper is then cooled and the gelatin allowed to congeal. The indicator paper may be stored at this point for an indefinite period of time, preferably under low light conditions, with care to avoid drying out of the gelatin. The indicator paper is then placed on a glass plate which has a larger surface area than the indicator paper. A bead of stopcock grease is run around the border of the indicator paper and the test film is smoothed over both the paper and bead. The plate is placed in a bag having a high barrier to oxygen and a vacuum drawn. This step serves the dual purpose of withdrawing as much oxygen as possible from the plate (support, indicator and test film) and also forces the stopcock grease to form a seal between the test film and support. After vacuum treatment, the plates are stackable and easy to handle.

The plate is then photoreduced by exposure to strong UV or visible light while still in the vacuum bag. When the test is started, the bag is removed and the plate is exposed to ambient, low light conditions. After a given period of time, the plate is again exposed briefly to UV light. Areas of relatively high permeability are seen as bright spots against a dark background. If desired, quantitative resolution of oxygen permeability can be had using known fluorescent detection methods.

One of ordinary skill in the art will readily recognize that this test is adaptable to a variety of materials and conditions. For example, the test method as written is convenient for use with transparent films having an oxygen transmission rate of about 0.001-200 cc/m$^2$ (atm°day). Objects with higher oxygen permeability can be tested using a lower concentration of oxygen in the test gas mix. Objects with very low oxygen permeability could be tested without ever removing the vacuum bag. The films described in this application are transparent, and fluorescence readings were taken from the sample side of the plates. Non-transparent objects (such as printed bags or aluminum foil) can also be tested using a transparent support. In that case, fluorescence readings are taken from the support side of the plate.

The following examples illustrate the use of the invention described herein without limiting its scope or the scope of the claims which follow.

EXAMPLE 1

Comparison of LOTIS and Standard Instrument Data

Raw values for oxygen transmission of the same 50 cm$^2$ areas of four samples of different oxygen barrier films were compared using the present invention (LOTIS) and an Ox-Trans™ 1000 unit from Modern Controls, Inc., Minneapolis, Minn.

A gel was made incorporating an oxidation-reduction system with riboflavin as the oxidizable substrate and sodium EDTA as a reducing aid during the photo-reduction process. The recipe for the gel was as follows:

| | |
|---|---|
| Gelatin | 7 grams/100 mls water |
| Disodium EDTA | 300 milligrams/100 mls water |
| Riboflavin | 20 milligrams/100 mls water |
| Antifoam B | 1 drop (to prevent foaming of solution) |

The EDTA was dissolved in the water first, using a magnetic stirrer and slight heat. After the EDTA was completely dissolved, the gelatin was added, leaving the beaker on slight (low) heat. When the gelatin was fully hydrated and dissolved, the riboflavin was added. The mixture was stirred until the riboflavin appeared well mixed, and then poured into a shallow, slightly heated double boiler apparatus. Pieces of absorbent paper 3MM CHR™ chromatographic paper, non-fluorescent, from Scientific Products, Charlotte, N.C., were placed in the double boiler and allowed to soak up the gel. The object was to keep the gel warm so that it will not set before the paper medium has been impregnated, but not to burn or scorch the gel. After the absorbent paper had been impregnated with the warm gel, the excess gel was gently removed from the medium using a roller, and the impregnated paper was placed in a refrigerator to allow the gel to set.

The indicator strips were dampened on both sides with an atomizer and affixed to glass plates. A bead of stopcock (vacuum) grease was run around the edge of the strip. A border of double-sided tape was run around the very outer edge of the glass plate to aid in sealing the test material to prevent oxygen leakage. The prepared plates were vacuum packaged in a plastic pouch which has a high barrier to oxygen transmission and photoreduced under fluorescent lights. The pouch was removed and a picture was taken to record the initial state of fluorescence of each plate. The exposed plates were placed in a dark cabinet for protection from light while they oxidized. Subsequent pictures of the oxidizing (and fluorescing) plates were taken at various time intervals and were digitally recorded using a computer and appropriate software. It should be appreciated that the light levels used to record the fluorescence were much less than those necessary to cause photoreduction.

When the plates were sufficiently fluorescent—after several (8 or more) hours of exposure or after "raw" fluorescence reading of over 200 analog-to-digital conversion units was reached—a circle of approximately 3.15 inches in diameter (approximately 7.8 sq. in. or 50 sq. cm) was drawn on the test material to mark the exact area for evaluating oxygen transmission by both the LOTIS method and the Ox-Trans unit. The mean pixel count (fluorescence level) of the test area at each time interval was determined using the appropriate software, and was repeated for all materials tested. These pixel counts were plotted on a graph versus time. The data in the "linear" portion of the graph were used to determine a "best-fit line" and linear regression equation shown in FIGS. 1-4. The slope of the regression equation="b" when the equation is in the form $Y=a+bx$ should be proportional to the oxygen transmission rate of the material.

The oxygen transmission rates of the test areas were determined using an Ox-Trans 1000™ unit according to standard procedure.

An initial period of non-linearity that was typical of each given type of material was observed. Without being held to any particular theory, it is believed this period represents the set-up of steady-state oxygen permeation through the film. Once the system had equilibrated, however, the fluorescence increased linearly with time, as expected.

The data for each sample is listed in Table 1 below. The average rate of transmission over a period of time for each sample as found by LOTIS method was compared to the single value per item obtained by the standard instrument. The LOTIS units are reported as fluorescent units/hr. The raw data had to be calibrated to correct for the camera and lens sensitivity. The system is less sensitive around the edges. Consequently, the correction can be made either physically or mathematically using a dome-shaped function that is characteristic for a given lens. Correlation among individual samples for each type of material was good.

Figure 5:
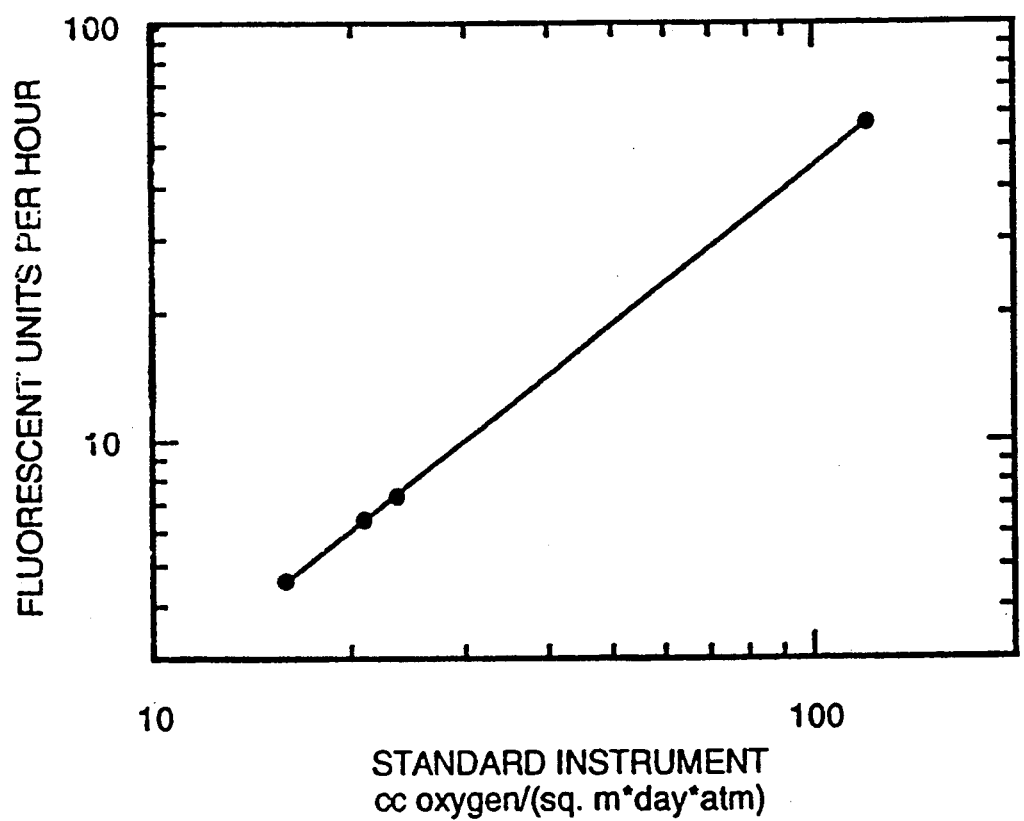
FIG. 5 is a comparison of Lotis and OTC data in fluorescent units per hour.

The four different materials each had different overall rates of oxygen transmission. When these overall rates are compared to the instrumental data using a log plot, a linear result with a high correlation coefficient (R-0.99997) was reported (See FIG. 5).

In sum, these experiments show that correlation between the LOTIS system and the standard instrument may be close enough to use for quantitative applications.

TABLE 1

| Sample | Standard Instrument (cc/m$^2$/24 hours @ 73° and 0% RH) | LOTIS FLuorescent Units*/hour |
|---|---|---|
| A-1 | 119.3 | 57.0 |
| -2 | 122.3 | 59.3 |
| -3 | 120.4 | 53.1 |
| B-1 | 23.3 | 7.0 |
| -2 | 22.7 | 7.2 |
| -3 | 24.5 | 7.8 |
| C-1 | 20.4 | 6.5 |
| -2 | 20.8 | 5.8 |
| -3 | 21.6 | 7.0 |
| D-1 | 15.9 | 4.3 |
| -2 | 15.7 | 4.6 |
| -3 | 14.9 | 4.9 |

*Corrected for camera lens sensitivity calibrated dome-shaped function (in text).

EXAMPLE 2

Detection of Damage

Figure 6:
FIG. 6 is a photograph of a damaged oxygen barrier film.

FIG. 6 is a photograph of an experimental 1 mil polyester film (E) coated with 1000 Angstroms (0.1 micron) of silica, which serves as an oxygen barrier. This film was deliberately creased in order to disrupt the silica coating. The fluorescing line marked by the arrow corresponded to the location of the crease.

EXAMPLE 3

Detection of a Manufacturing Flaw

Figure 7:
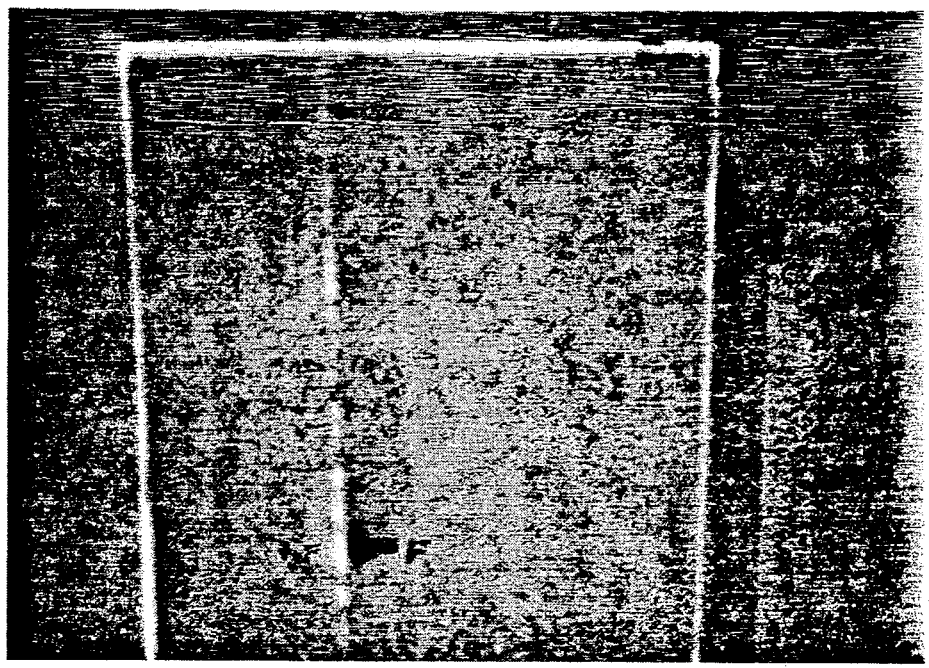
FIG. 7 is a photograph of a film sample with a manufacturing flaw.
Figure 8:
FIG. 8 is a photograph of a microscopic cross section of the film of FIG. 7 in the region of the flaw.

A sample of four-layer oxygen barrier film that showed a highly fluorescent streak when tested using the LOTIS system was subjected to microscopic examination. FIG. 7 is a photograph of the fluorescing plate. FIG. 8 is a photograph of a microscopic cross section of the same material in the region of the fluorescing streak. Zone 1 shows the intact four layer structure about 1.7 mils thick from the non-fluorescent area marked "NF" on FIG. 7. The layers were as follows:

---
1 — Sealant — poly(ethylene vinyl acetate)/polyolefin blend, nominally 0.3 mils
2 — Oxygen Barrier — poly(vinylidene dichloride methyl acrylate), nominally 0.16 mils
3 — Core — poly(ethylene vinyl acetate), 1.04 mils ---
-continued
---
4 — Outer — acrylate copolymer, .47 mils.

Zone II shows a thinning of layers 1 and 2. Zone III shows the absence of layers 1 and 2. Zone III is taken from the highly fluorescent area marked "F" on FIG. 6.

This technique can also be useful to detect extrusion variations of the oxygen barrier materials that are not, strictly speaking, flaws in a given material. The technique can be used as a tool to analyze variations in layer thickness, uniformity of blending and peculiarities of starting and stopping of extrusion. When the barrier is deposited on a surface, deposition patterns can be detected, to the extent they are related to oxygen permeability.

What is claimed is:

1. A method of detecting the permeability of an article to oxygen, comprising the steps of:
   dispersing a redox indicator in a carrier;
   placing the article on the carrier;
   removing residual oxygen from the carrier and the article;
   photoreducing the redox indicator;
   exposing the article to oxygen;
   exposing the redox indicator to light for visualization of redox changes to determine the permeability of the article to oxygen.

2. The method of claim 1, wherein the redox indicator is fluorescent in its oxidized state.

3. The method of claim 1, wherein the redox indicator can be photoreduced in its oxidized form.

4. The method of claim 1, wherein the redox indicator is riboflavin.

5. The method of claim 1, wherein the carrier comprises gelatin, agar or glycerol.

6. The method of claim 1, wherein the carrier further comprises a reducing agent.

7. The method of claim 1, wherein the reducing agent is selected from the group consisting of sodium or calcium ethylenediaminetetracetic acid, sodium or calcium citrate, triethylamine or a riboflavin derivative.

8. The method of claim 1 additionally comprising the step of substantially lowering the initial oxygen content of the carrier and test article by purging with an inert gas or evacuation, or both, before the photoreducing step.

9. A method of detecting the permeability of an article to oxygen, comprising the steps of:
   dispersing a redox indicator in a carrier; placing the carrier on a support placing the article on the carrier and opposite the support wherein the redox indicator is distributed between the test article and the support;
   removing residual oxygen from the carrier and test article;
   photoreducing the redox indicator;
   exposing the article to oxygen;
   exposing the redox indicator to light for visualization of redox changes to determine the permeability of the article to oxygen.

* * * * *